United States Patent
Sharma et al.

(10) Patent No.: US 11,532,395 B2
(45) Date of Patent: Dec. 20, 2022

(54) OPTIMIZING CATHETERIZATION LABORATORY THROUGHPUT USING MACHINE LEARNING

(71) Applicant: Siemens Healthcare GmbH, Erlangen (DE)

(72) Inventors: Puneet Sharma, Princeton Junction, NJ (US); Lucian Mihai Itu, Brasov (RO); Tiziano Passerini, Plainsboro, NJ (US)

(73) Assignee: Siemens Healthcare GmbH, Erlagen (DE)

( * ) Notice: Subject to any disclaimer, the term of this patent is extended or adjusted under 35 U.S.C. 154(b) by 558 days.

(21) Appl. No.: 16/282,343

(22) Filed: Feb. 22, 2019

(65) Prior Publication Data

US 2020/0273569 A1     Aug. 27, 2020

(51) Int. Cl.
| | |
|---|---|
| *G06N 20/00* | (2019.01) |
| *G16H 50/20* | (2018.01) |
| *G06N 5/04* | (2006.01) |
| *G16H 10/60* | (2018.01) |
| *G16H 30/40* | (2018.01) |
| *G06N 3/08* | (2006.01) |

(52) U.S. Cl.
CPC ............ *G16H 50/20* (2018.01); *G06N 5/04* (2013.01); *G06N 20/00* (2019.01); *G16H 10/60* (2018.01); *G16H 30/40* (2018.01); *G06N 3/08* (2013.01)

(58) Field of Classification Search
CPC ............ G06N 20/00; G06N 5/04; G06N 3/08; G06N 3/006; G16H 50/20; G16H 10/60; G16H 30/40; G16H 20/40; G16H 40/20

USPC .......................................................... 706/12
See application file for complete search history.

(56) References Cited

U.S. PATENT DOCUMENTS

| | | | | |
|---|---|---|---|---|
| 2004/0122719 | A1* | 6/2004 | Sabol | G06Q 10/06315 705/7.13 |
| 2007/0067194 | A1* | 3/2007 | Danehorn | G06Q 10/02 705/5 |
| 2007/0203761 | A1* | 8/2007 | Keen | G16H 50/70 705/5 |
| 2008/0221830 | A1* | 9/2008 | Ilkin | G06F 19/00 702/176 |
| 2012/0307964 | A1* | 12/2012 | Hall | A61B 6/03 378/8 |
| 2013/0185090 | A1* | 7/2013 | Kargar | G16H 40/63 705/2 |

(Continued)

OTHER PUBLICATIONS

Itu, "A machine-learning approach for computation of fractional flow reserve from coronary computed tomography", J Appl Physiol 121: 42-52, 2016. (Year: 2016).*

(Continued)

*Primary Examiner* — Dave Misir (57) ABSTRACT

Systems and methods for determining one or more measures of interest for optimizing throughput of a catheterization laboratory are provided. A priori medical procedure data relating to a medical procedure to be performed on a patient in a catheterization laboratory is received. One or more measures of interest are predicted based on the received a priori medical procedure data using a trained machine learning model. The one or more measures of interest include an overall time for performing the medical procedure on the patient in the catheterization laboratory. The one or more predicted measures of interest are output.

20 Claims, 5 Drawing Sheets

(56) References Cited

U.S. PATENT DOCUMENTS

| | | | |
|---|---|---|---|
| 2017/0035514 A1* | 2/2017 | Fox | G06Q 10/10 |
| 2018/0253531 A1* | 9/2018 | Sharma | G06K 9/6282 |
| 2019/0013095 A1* | 1/2019 | Lawrie | G06Q 10/06311 |
| 2019/0180868 A1* | 6/2019 | Makram | G06Q 10/0631 |
| 2020/0211692 A1* | 7/2020 | Kalafut | G06N 20/00 |

OTHER PUBLICATIONS

Itu, "A machine-learning approach for computation of fractional flow reserve from coronary computed tomography", J Appl Physiol 121: 42-52, 2016. (Previously supplied). (Year: 2016).*

European Search Report dated Sep. 2, 2019 in corresponding European Patent Application No. 19464002.5.

Reed et al., "Operational Efficiency and Productivity Improvement Initiatives in a Large Cardiac Catheterization Laboratory", JACC: Cardiovascular Interventions, Jan. 2018, 10 pgs.

Schweikhart et al., The Applicability of Lean and Six Sigma Techniques to Clinical and Translational Research, J Investig Med., Oct. 2009, 15 pgs.

Bartak et al., "Constraint Satisfaction Techniques in Planning and Scheduling", Journal of Intelligent Manufacturing, Feb. 2010, vol. 21, Issue 1, 12 pgs.

Li et al., "Deep Reinforcement Learning: An Overview", https://arxiv.org/abs/1701.07274, Jan. 25, 2017, 30 pgs.

Tofield, A., "Cold Weather and Myocardial Infarction" European Heart Journal, vol. 38, Issue 3, Jan. 14, 2017. p. 140.

Gentry et al., "Defining Health in the Era of Value-based Care: Lessons from England of Relevance to Other Health System", Cureus, 2017, 9 pgs.

Brimmer, Kelsey, "Cut Labor Costs with Smarter Scheduling", http://www.healthcarefinancenews.com, Healthcare Finance News, Sep. 13, 2013.

"Cardiovascular Diseases (CVDs)", World Health Organization, Fact Sheet, May 17, 2017, 6 pgs.

* cited by examiner

OPTIMIZING CATHETERIZATION LABORATORY THROUGHPUT USING MACHINE LEARNING

TECHNICAL FIELD

The present invention relates generally to optimizing catheterization laboratory throughput, and more particularly to optimizing catheterization laboratory throughput by predicting overall procedure time using machine learning.

BACKGROUND

With the increasing cost of healthcare, the healthcare financial model has been shifting from a fee-for-service model to a value-based care model. Thus, hospitals are increasingly being reimbursed or compensated based on the quality of the services that they perform, instead of being reimbursed based only on the quantity and type of services that they perform. This shift in the healthcare financial model is expected to continue and likely accelerate in the coming years. In order for hospitals to maximize reimbursements under the value-based care model, hospitals will need to become high-performing units by reducing risk-adjusted mortality, risk-adjusted readmission rates, and costs. Within the cost structure of a hospital, labor costs may represent up to 60% of total costs, and therefore any decrease in labor costs while maintaining the quality of care is valuable.

In the context of cardiovascular disease, catheterization laboratories ("cath labs") represent one of the most important, but complex, units for diagnosis and treatment under the value-based care model. Cath labs involve a number of aspects that contribute to such complexity, such as the number of different types of staff (e.g., interventionalists, nurses); equipment (e.g., x-ray angiography systems, health monitoring systems, intravascular imaging tools (e.g., intravascular ultrasound, optical coherence tomography), intravascular measurement systems (e.g., fractional flow reserve measurement systems), visualization workstations, post-processing workstations, electronic health records recording systems, etc.); consumables; and procedures (e.g., interventions for stable or acute patients, resolving chronic total occlusions, follow-up examinations). This complexity makes it difficult to improve the cost effectiveness of cath labs under the value-based care model.

In one conventional approach to improve cost-effectiveness in cath labs, workflows of a cath lab are analyzed to remove all unnecessary steps, and only those steps which add value and serve the patient's or clinician's needs are retained. Under this conventional approach, workflow optimization is achieved by skill matching, reducing the number of steps to perform tasks, and increasing the use of electronic and computer-based systems. In other words, this conventional approach is mostly based on the application of pre-defined rules according to a static model of optimal operation. This does not allow the required flexibility to adapt to the large number of variants determined both by patient-related as well as by non-patient-related circumstances.

BRIEF SUMMARY OF THE INVENTION

In accordance with one or more embodiments, systems and methods for determining one or more measures of interest for optimizing throughput of a catheterization laboratory are provided. A priori medical procedure data relating to a medical procedure to be performed on a patient in a catheterization laboratory is received. The a priori medical procedure data is available before the medical procedure is performed on the patient in the catheterization laboratory. One or more measures of interest are predicted based on the received a priori medical procedure data using a trained machine learning model. The one or more measures of interest include an overall time for performing the medical procedure on the patient in the catheterization laboratory. The one or more predicted measures of interest are output.

In one embodiment, the medical procedure data comprises patient related medical procedure data. The patient related medical procedure data comprises one or more of: medical images of the patient, measures extracted from the medical images of the patient, vascular access of the patient, a likelihood of the patient requiring intravascular imaging, a likelihood of the patient requiring invasive measurements, a type of the patient, laboratory test results of the patient, demographic information of the patient, and a history of the patient.

In one embodiment, the medical procedure data comprises non-patient related medical procedure data. The non-patient related medical procedure data comprises one or more of: availability of medical professionals, devices used in the catheterization laboratory, a time associated with the medical procedure, and medical professionals scheduled to perform the medical procedure.

In one embodiment, the one or more measures of interest further comprise a time for performing specific portions of the medical procedure or a complexity score associated with performing the medical procedure on the patient in the catheterization laboratory.

In one embodiment, guidelines for performing the medical procedure to reduce the overall time for performing the medical procedure on the patient in the catheterization laboratory are generated using the trained machine learning model. The guidelines include one or more of: acquisition angles for acquiring medical imaging of the patient, an order for investigating coronary arteries of the patient, which coronary arteries are to be investigated, types of medical devices to be used during the medical procedure, whether intravascular imaging is required, and a location for vascular access of the patient.

In one embodiment, guidelines for performing the medical procedure to reduce resource usage during the medical procedure on the patient in the catheterization laboratory are generated using the trained machine learning model. The guidelines include one or more of: an order for investigating coronary arteries of the patient, a number of medical devices to be used during the medical procedure, and a number and type of medical professionals needed for performing the medical procedure.

In one embodiment, resources for performing the medical procedure on the patient in the catheterization laboratory are automatically scheduled based on the predicted one or more measures of interest using a trained artificial intelligence agent.

In one embodiment, the one or more predicted measures of interest are displayed on a display device.

These and other advantages of the invention will be apparent to those of ordinary skill in the art by reference to the following detailed description and the accompanying drawings.

DETAILED DESCRIPTION

The present invention generally relates to optimizing catheterization laboratory throughput using machine learning. Embodiments of the present invention are described herein to give a visual understanding of such systems and methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to predicting an overall time for performing a medical procedure to optimize catheterization laboratory ("cath lab") throughput, the present invention is not so limited. Embodiments of the present invention may be applied for predicting any measure of interest to optimize throughput of any unit in a hospital, or even to optimize any process or workflow in the medical or non-medical field.

Figure 1:
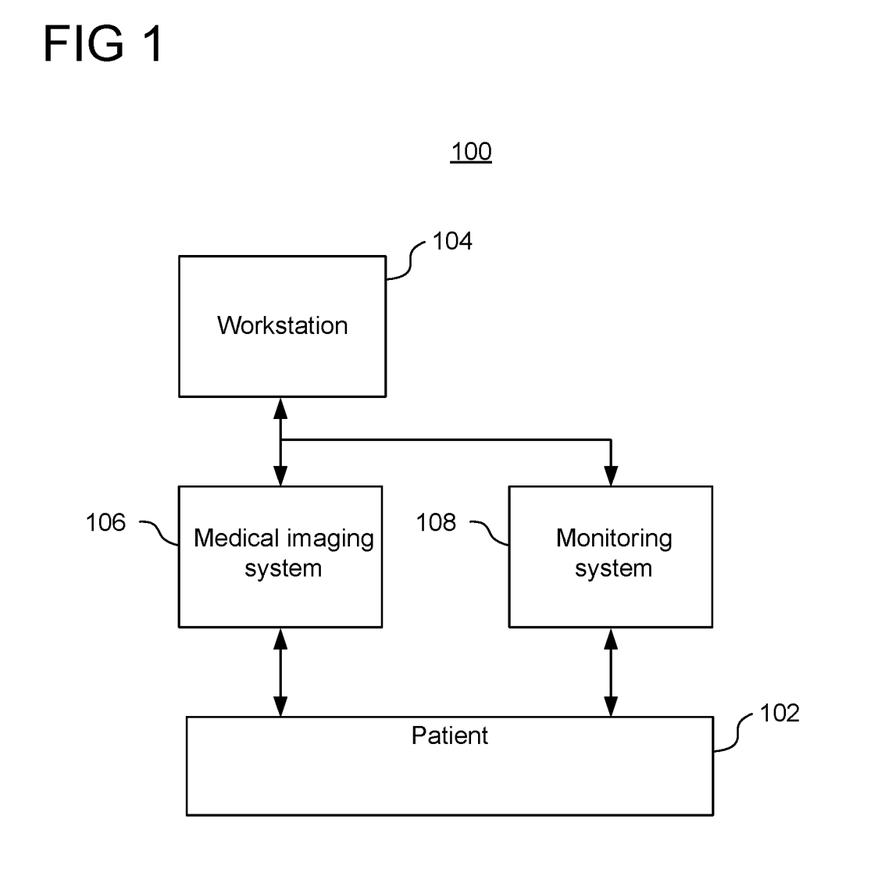
FIG. 1 shows an illustrative catheterization laboratory environment.

FIG. 1 shows a cath lab environment 100 for performing a medical procedure on a patient 102. For example, the medical procedure may be an evaluation or treatment of patient 102 for a cardiovascular disease such as coronary artery disease. Prior to performing the medical procedure on patient 102 in cath lab environment 100, a number of different resources for performing the medical procedure are scheduled. Such resources for performing the medical procedure may include, for example, a number and type of medical professionals (e.g., doctors or nurses), medical equipment, and consumables (e.g., drugs).

Exemplary medical equipment includes, for example, one or more workstations 104, one or more medical imaging systems 106, and one or more monitoring systems 108 for performing the medical procedure on patient 102. Workstation 104 may be, e.g., a visualization workstation, a post-processing workstation, an electronic health record system, and/or any other suitable workstation. Workstation 104 may be implemented using any suitable computing device, such as, e.g., computer 502 of FIG. 5. Medical imaging system 106 may be, e.g., an x-ray angiography system, an intravascular imaging system (e.g., intravascular ultrasound (IVUS) or optical coherence tomography (OCT) system), and/or an imaging system of any other suitable modality or combination of modalities. Monitoring system 108 may be, e.g., a health monitoring system or a measurement system (e.g., an intravascular fractional flow reserve measurement system). It should be understood that cath lab environment 100 may include additional resources to be scheduled for performing a medical procedure on patient 102, and that cath lab environment 100 is a high level representation of a cath lab for illustrative purposes.

Scheduling resources for performing the medical procedure on patient 102 in cath lab environment 100 is a complex task due to the uncertainty associated with the resources required for performing the medical procedure on patient 102. One uncertainty associated with scheduling resources is the overall time for performing the medical procedure on patient 102. Knowing the overall time for performing the medical procedure is important for optimally scheduling medical professionals, preparing and configuring medical equipment, and preparing consumables to optimize (e.g., maximize) cath lab throughput to thereby increase reimbursements under the value-based care model. Advantageously, the embodiments described herein provide for a machine learning model trained to predict the overall time for performing a medical procedure (or other measures of interest) based on a priori information (i.e., information available before the medical procedure).

Figure 2:
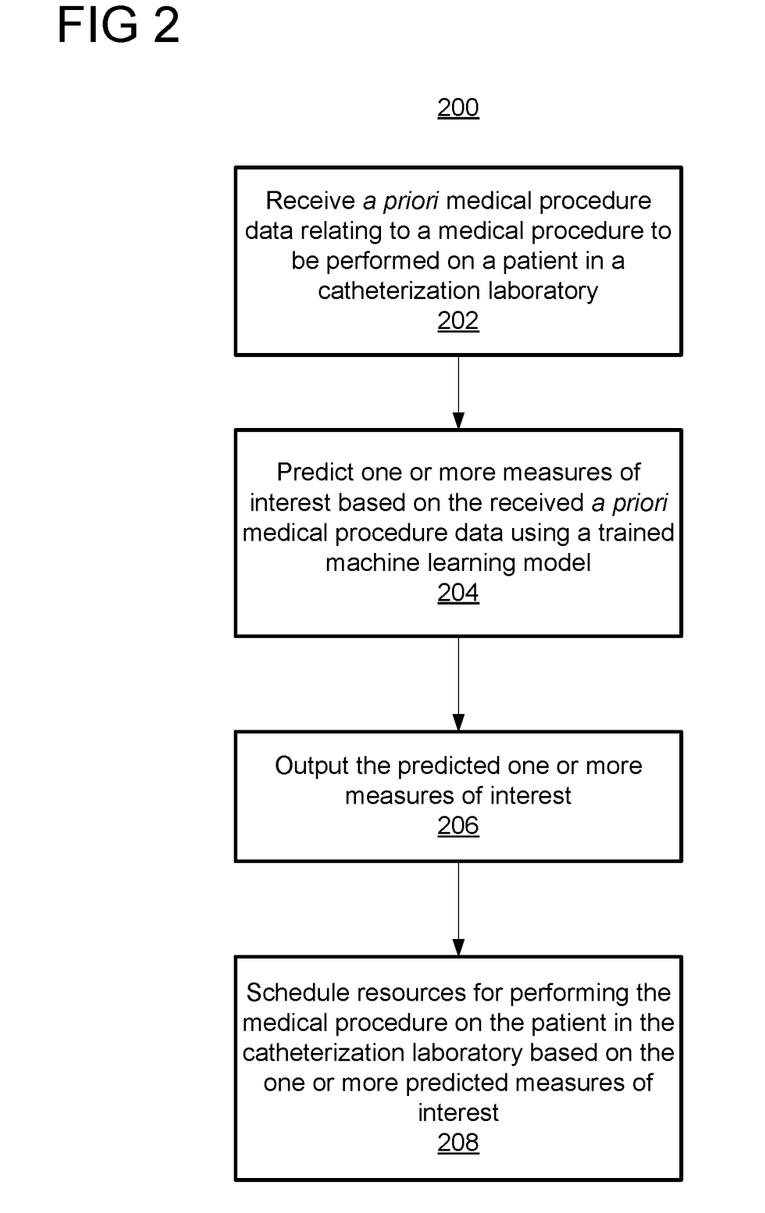
FIG. 2 shows a method for optimizing catheterization laboratory throughput based on one or more measures of interests predicted by a trained machine learning model, in accordance with one or more embodiments.

FIG. 2 shows a method 200 for optimizing cath lab throughput based on one or more measures of interests predicted by a trained machine learning model, in accordance with one or more embodiments. Method 200 may be performed by any suitable computing device, such as computer 502 of FIG. 5.

At step 202, a priori medical procedure data relating to a medical procedure to be performed on a patient in a catheterization laboratory is received. In one embodiment, the a priori medical procedure data is medical procedure data available before the medical procedure is performed on the patient in the catheterization laboratory. The a priori medical procedure data may comprise patient related medical procedure data and non-patient related medical procedure data.

The patient related medical procedure data may comprise one or more of: 1) a priori acquired medical images of the patient, such as, e.g., cardiac computed tomography angiography (CCTA) images, MRI images, and myocardial perfusion imaging (MPI) images acquired during prior medical exams; 2) measures extracted (automatically or manually) from a priori acquired medical images of the patient, such as, e.g., a number of lesions, a SYNTAX score of the lesions, an anatomical severity of the lesions, a hemodynamic severity of the lesions (e.g., as assessed based on a computed fractional flow reserve (FFR)), plaque characteristics (e.g., plaque morphology), a type of the lesions (e.g., single branch, focal/diffuse, bifurcation, left main, distal, etc.), and disease complexity (more tortuous or calcified vessel in the access path will require more time); 3) radiology reports relating to a priori acquired medical images of the patient, such as, e.g., features extracted (manually or automatically using natural language processing) from the radiology report; 4) vascular access of the patient, such as, e.g., the likelihood of radial access success accessed a priori; 5) likelihood of the patient requiring intravascular imaging (e.g., OCT or IVUS imaging); 6) likelihood of the patient requiring invasive measurements (e.g., invasive pressure measurements, such as FFR or instantaneous wave-free ratio (iFR)); 7) non-invasive stress tests of the patient; 8) a type or classification of the patient, such as, e.g., stable, acute coronary syndrome (ACS) (e.g., ST elevation myocardial infarction (STEMI), non-ST elevation myocardial infarction (NSTEMI), or unstable angina (UA)), or chronic total occlusion; 9) laboratory test results of the patient, such as, e.g., troponin levels for ACS patients; 10) demographic information of the patient, such as, e.g., age, ethnicity, gender, weight, height, race, body mass index, diabetes, hypertension, hypercholesterolemia, smoking history, family history of coronary artery disease, prior myocardial infarction, prior coronary arterial bypass graft, angina type (e.g., stable, worsening, silent ischemia, or any other angina category as defined by the Canadian cardiovascular society, American heart association, American college of cardiology, or any other clinically accepted guidelines); 11) history of the patient, such as, e.g., clinical history or medication history; 12) other co-morbidity diseases of the patient; and 13) characteristics related to post-procedural hemostasis, such as, e.g., bleeding disorders (e.g., hemophilia or immune thrombocytopenia, HELLP syndrome, hemolytic-uremic syndrome, etc.).

The non-patient related medical procedure data may include one or more of: 1) the availability of medical professionals (e.g., doctors or nurses) for performing the medical procedure on the patient in the cath lab; 2) the angiography system or configuration of the angiography system used in the cath lab; 3) the type of devices used (e.g., the type of guidewire used and preferred); 4) the time associated with the medical procedure (e.g., the time, day of the week, season, etc. that the medical procedure is scheduled to be performed); and 5) the particular medical professionals scheduled to perform the medical procedure.

At step 204, one or more measures of interest are predicted based on the received a priori medical procedure data using a trained machine learning model. The trained machine learning model may be trained during a prior offline or training stage, e.g., according to the steps 302-308 of workflow 300 of FIG. 3 and applied at step 204 during an online or testing stage according to steps 310-316 of workflow 300 of FIG. 3.

The machine learning model may be any suitable machine learning model. In one embodiment, the machine learning model may be based on a fully connected neural network, in which the received a priori medical procedure data is provided as an input to the first layer of neurons of the network. The neural network comprises a series of layers, with each layer comprising a number of neurons and each neuron being connected to every neuron in the previous layer. The measures of interest are returned by the network in the last layer of neurons, as the result of a combination of the activation levels of the neurons in previous layers. The weights of this combination are learned during the training stage, e.g. as the ones that yield the most accurate mapping between input features and output measures, based on the available training data. In another embodiment, the machine learning model may be based on convolutional neural networks, in which case some of the deeper layers comprise neurons that are connected to a subset of neurons in the previous layer. The combination of activation values of the subset of neurons in the previous layer determines the activation of the neuron connected to them. The weights of such a combination are learned during the training stage.

The one or more measures of interest may include any measure of interest suitable for scheduling resources for performing the medical procedure on the patient in the cath lab to optimize throughput of the cath lab. In one embodiment, the one or more measures of interest may include an overall time for performing the medical procedure on the patient in the cath lab. In another embodiment, the one or more measures of interest may include a time for performing specific portions of the medical procedure. The specific portions of the medical procedure may include, e.g., a patient preparation portion (e.g., for determining intravenous access of the patient, performing a medical review of the patient, obtaining consent from the patient, etc. obtained outside of the cath lab), a procedure start portion (e.g., for administering sedation or local anesthesia, performing vascular access, etc.), an actual procedure portion, and a case completion portion (e.g., for performing hemostasis or assessing vital signs of the patient). In another embodiment, the one or more measures of interest may include a complexity score associated with performing the medical procedure on the patient in the cath lab. The complexity score may be used, for example, by higher order systems to schedule resources for performing the medical procedure on the patient in the cath lab. In one embodiment, the higher order systems include artificial intelligence agent 402 of FIG. 4, as discussed in further detail below.

In one embodiment, the trained machine learning model also generates personalized guidelines, before the medical procedure is performed, for performing the medical procedure on the patient in the cath lab to minimize the overall time of the medical procedure using the a priori medical procedure data. Such guidelines can be generated for instance by one or more machine learning algorithms, trained to output measures of interest according to a certain policy. This can be posed as a classification problem, and the neural network is trained to classify output measures as satisfying or violating the policy. During the training stage, positive and negative examples are presented to the network.

In one embodiment, the guidelines may define acquisition angles to be used for acquiring medical imaging of the patient. Standard acquisition angles may result in significant overlap and foreshortening of coronary arteries, which may lead to longer procedure times, higher quantities of contrast agent administered into the patient's arteries, and higher overall radiation exposure to the patient and the medical professionals. By using a prior information of the patient from non-invasive imaging techniques (e.g., CCTA), the structure or configuration of the coronary arteries can be determined and the optimal acquisition angles for minimizing overlap and foreshortening can be determined therefrom. The optimal acquisition angles can be defined as angle values within the range associated with the "optimal" class. Other classes are associated with different ranges of angle values.

In another embodiment, the guidelines may define an order in which to investigate the coronary arteries (e.g., right coronary artery first or left coronary artery first). In still another embodiment, the guidelines may define which of the coronary arteries are to be investigated. For example, if the right coronary artery appears to be healthy on non-invasive imaging of the patient, then no invasive imaging of the right coronary artery is required and procedure time can be reduced. In another embodiment, the guidelines may define which types of stents (or other medical devices) are likely to be required during the medical procedure, allowing the stents to be prepared prior to the procedure to reduce procedure time. In another embodiment, the guidelines may define whether intravascular imaging is required so that the corresponding equipment can be prepared prior to the procedure, reducing procedure time. In yet another embodiment, the guidelines may define a location which may or may not be suitable for vascular access. For example, the guidelines may indicate if radial access is likely to be unsuitable for the intervention, reducing procedure time by the time that would have been spent trying to gain access through the radial artery.

In one embodiment, the trained machine learning model also generates guidelines, before the medical procedure is performed, on how to optimize resource usage in the cath lab using the a priori medical procedure data. In one embodiment, the guidelines may indicate an order of investigating coronary artery branches so as to minimize the usage of contrast agent and the usage of hyperemia inducing drugs (e.g., adenosine). For example, the guidelines may indicate whether intracoronary boluses of adenosine may suffice, or if intravenous administration is required (which increases both procedure time and the amount of adenosine being used). In one embodiment, the guidelines may define an optimized number of guidewires (or other medical devices) to be used. In one embodiment, the guidelines may indicate the number and type of medical professionals (e.g., interventionalists, nurses, etc.) required for the medical procedure, e.g., based on the complexity of the medical procedure.

While step 204 is described as using a trained machine learning model to predict the one or more measures of interest, it should be understood that other approaches may also be employed, such as, e.g., a rule-based approach.

At step 206, the one or more predicted measures of interest are output. The one or more predicted measures of interest can be output by displaying the one or more predicted measures of interest on a display device of a computer system, storing the one or more predicted measures of interest on a memory or storage of a computer system, or by transmitting the one or more predicted measures of interest to a remote computer system. In one embodiment, the one or more predicted measures of interest are output to another system for further processing.

At step 208, resources for performing the medical procedure on the patient in the cath lab are scheduled based on the one or more predicted measures of interest. In one embodiment, a higher order system, such as, e.g., artificial intelligence (AI) agent 402 of FIG. 4, described in further detail below, automatically schedules resources for performing the medical procedure on the patient in the cath lab to optimize throughput of the cath lab.

While method 200 is described at the patient level for scheduling resources for performing a medical procedure on a single patient, method 200 may alternatively be applied at a patient group level for scheduling resources for performing a medical procedure on a specific subgroup of patients. The specific subgroup of patients may be patients having similar characteristics, such as, e.g., stable patients with single vessel coronary artery disease (CAD).

Figure 3:
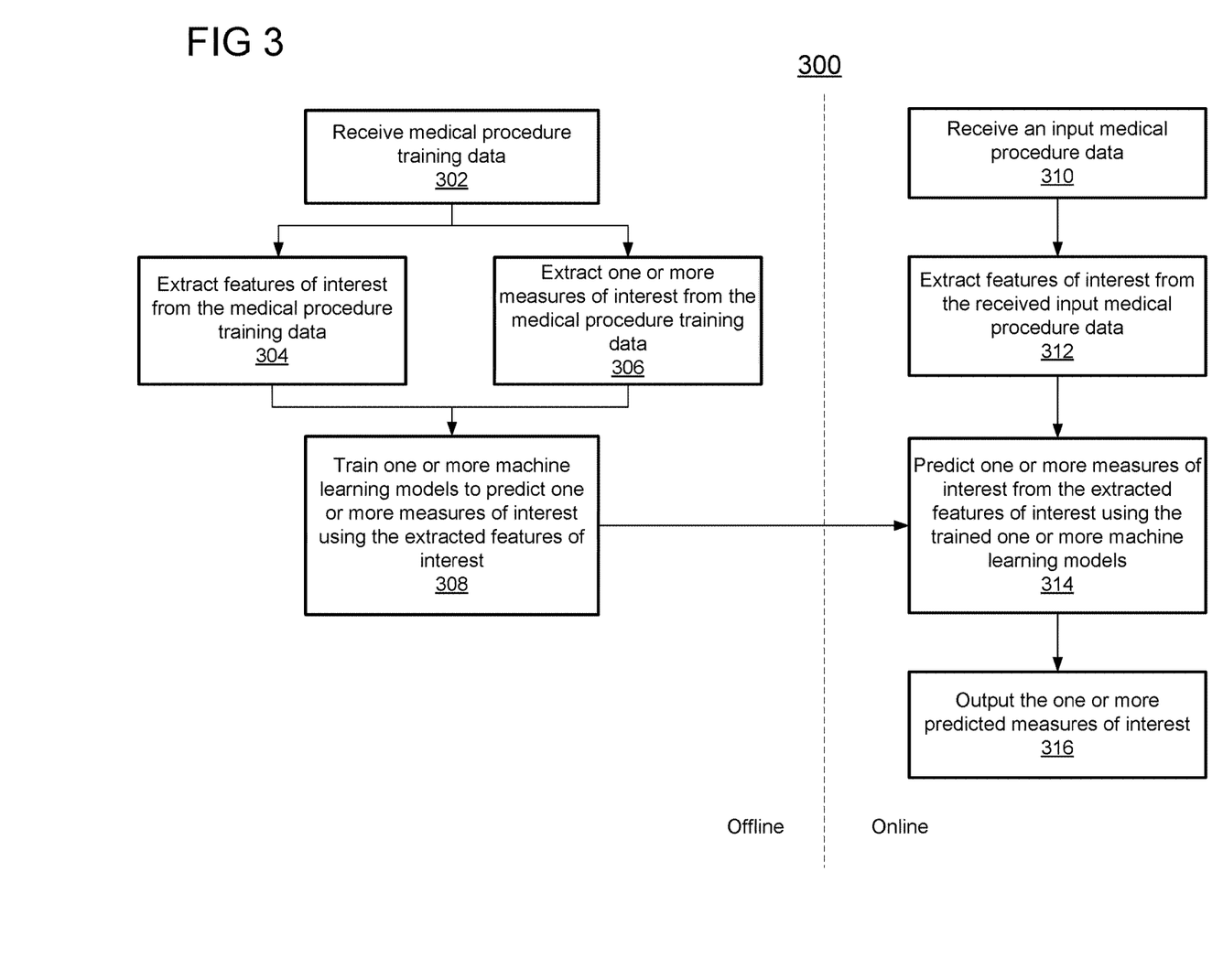
FIG. 3 shows a workflow for training and applying a machine learning model for predicting one or more measures of interest for optimizing catheterization laboratory throughput, in accordance with one or more embodiments.

FIG. 3 shows a workflow 300 for training and applying a machine learning model for predicting one or more measures of interest for optimizing cath lab throughput, in accordance with one or more embodiments. Steps 302-308 show an offline or training stage for training a machine learning model to predict one or more measures of interest for optimizing cath lab throughput and steps 310-316 show an online or testing stage for applying the trained machine learning model to predict the one or more measures of interest. In one embodiment, steps 312-314 of the testing stage may be performed at step 204 of FIG. 2 to apply the trained machine learning model to predict the one or more measures of interest.

During a training stage, at step 302, medical procedure training data is received. The medical procedure training data may be any training data suitable for training a machine learning model to predict one or more measures of interest for optimizing cath lab throughput. For example, the medical procedure training data may be similar to the medical procedure data as described above with respect to step 202 of FIG. 2, but also include information on the measures of interest to be predicted (e.g., the overall time of the medical procedure). In one embodiment, the medical procedure training data is actual patient data previously acquired.

At step 304, features of interest are extracted from the medical procedure training data. The features are determined based on characteristics available from the medical procedure training data. In one embodiment, a vector of features is defined to be provided as input to the one or more neural networks. Each feature is either a categorical or a quantitative variable. For instance, troponin levels from lab tests can be used as a quantitative variable in the feature vector; while the type of patient (stable, acute, etc) can be used as a categorical variable. For each subject a unique feature vector can thus be generated.

At step 306, one or more measures of interest are extracted from the medical procedure training data. The one or more measures of interest may include any measure of interest suitable for scheduling resources for performing the medical procedure on the patient in the cath lab to optimize throughput of the cath lab. In one embodiment, the one or more measures of interest include the measures of interest discussed above with respect to step 204 of FIG. 2. The one or more measures of interest may be extracted from the medical procedure training data using any suitable approach. In one embodiment, natural language processing may be used to extract the one or more measures of interest from the medical procedure training data. It should be understood that step 306 may be performed at any time prior to step 308 (e.g., before step 304, after step 304, or concurrently with (e.g., in parallel with) step 304).

At step 308, one or more machine learning models are trained to predict one or more measures of interest using the extracted features of interest. The machine learning models may include, e.g., a fully connected neural network, a convolutional neural network, or any other suitable machine learning model. The machine learning models may be trained using any suitable approach, such as, e.g., regression, instance-based methods, regularization methods, decision tree learning, Bayesian, kernel methods, clustering methods, association rule learning, artificial neural networks, dimensionality reduction, ensemble methods, etc. In one embodiment, the machine learning models are trained using deep learning. Deep learning generally refers to a machine learning technique using several information processing layers. Hierarchical structures are employed, either for learning features or representations, or for classification or regression.

During the online stage, at step 310, input medical procedure data is received. The input medical procedure data represents unseen data related to a medical procedure to be performed on a patient in a cath lab. The input medical procedure data may be any data suitable for predicting the one or more measures of interest by the trained machine learning model. For example, the input medical procedure data may be the medical procedure data as described above with respect to step 202 of FIG. 2.

At step 312, features of interest are extracted from the input medical procedure data.

At step 314, one or more measures of interest are predicted from the extracted features of interest using the trained one or more machine learning models. The one or more measures of interest are suitable for scheduling resources for performing the medical procedure on the patient in the cath lab to optimize throughput of the cath lab. In one embodiment, the one or more measures of interest include the measures of interest discussed above with respect to step 204 of FIG. 2.

At step 316, the one or more predicted measures of interest are output. The one or more predicted measures of interest can be output by displaying the one or more predicted measures of interest on a display device of a computer system, storing the one or more predicted measures of interest on a memory or storage of a computer system, or by transmitting the one or more predicted measures of interest to a remote computer system, e.g., for further processing (e.g., automatically scheduling based on the one or more predicted measures of interest).

In accordance with one embodiment, a scheduling system may automatically schedule resources for performing a medical procedure on a patient in a cath lab to optimize cath lab throughput based on one or more predicted measures of interest. In one example, the scheduling system may be employed at step 208 of FIG. 2 to automatically schedule resources based on the one or more predicted measures of interest. The scheduling system may be any system suitable for scheduling resources for performing a medical procedure on a patient in a cath lab. In one embodiment, the scheduling system is a higher order system, such as, e.g., an AI agent.

Figure 4:
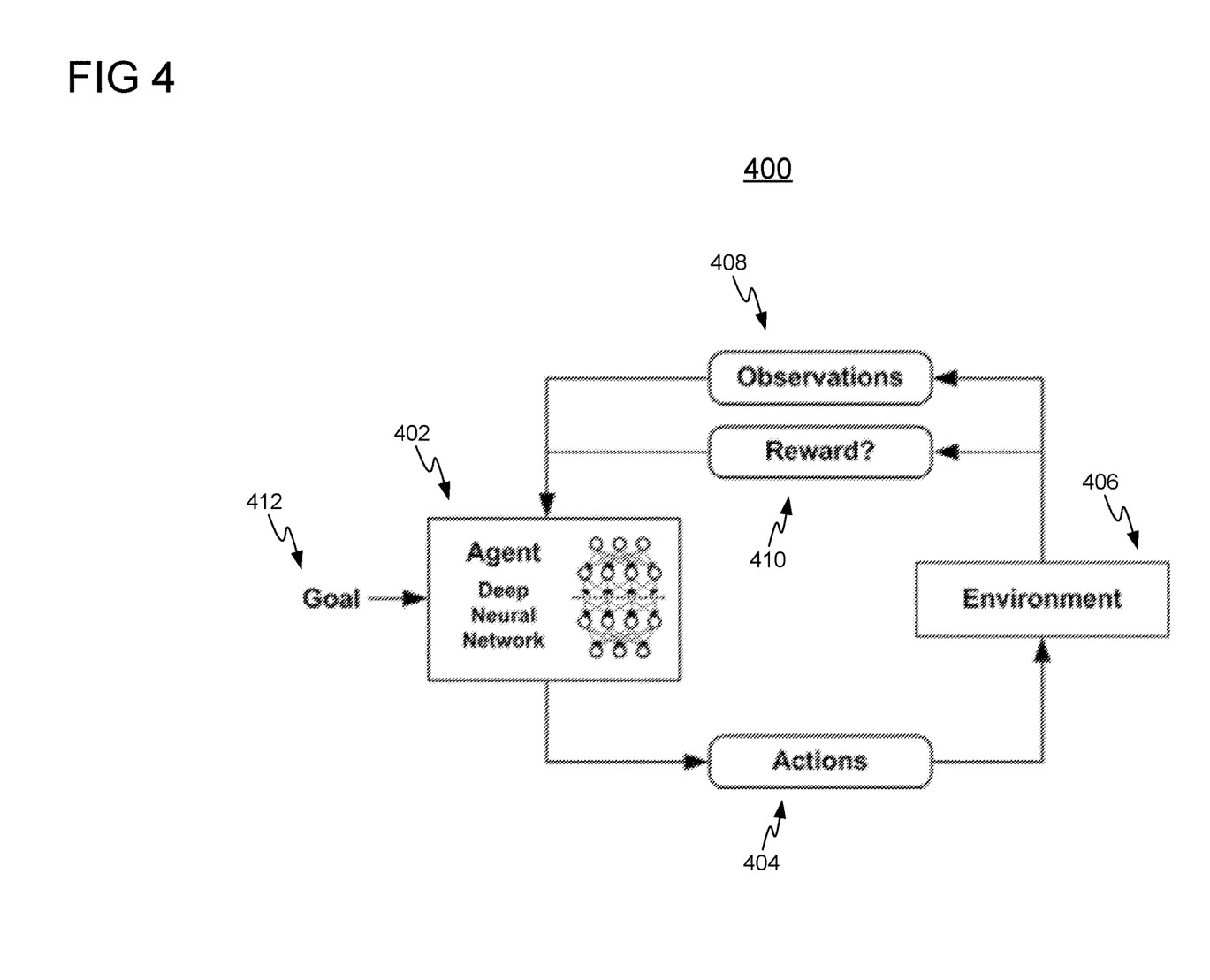
FIG. 4 shows a high level workflow for training an artificial intelligence agent for automatically scheduling resources for performing a medical procedure on a patient in a catheterization laboratory, in accordance with one or more embodiments.

FIG. 4 shows a high level workflow 400 for training an AI agent for automatically scheduling resources for performing a medical procedure on a patient in a cath lab, in accordance with one or more embodiments. In one embodiment, the trained AI agent 402, trained according to workflow 400, may be employed to automatically perform step 208 of FIG. 2.

During training, AI agent 402 performs a series of actions 404 in an environment 406. Actions 404 modify environment 406 such that environment 406 evolves either towards or away from the desired goal 412. AI agent 402 performs observations 408 of environment 406 and receives a reward 410 depending on the effectiveness of the performed actions 404. From the association of observations 408 and rewards 410, AI agent 402 learns a policy of action. Goal 412 may be the optimal scheduling of resources for performing a medical procedure on a patient in a cath lab. For example, optimal scheduling may be determining a good scheduling solution in near real time.

Environment 406 is defined by a set of inputs defining a cath lab environment for performing a medical procedure on a patient. For example, the set of inputs may define a number of available doctors, a number of possible patients, a number of available cath lab rooms, or any other suitable input describing the environment. In one embodiment, environment 406 includes one or more measures of interest, e.g., output at step 206 of FIG. 2. For example, environment 406 may include a complexity score representing a level of complexity of a medical procedure to be performed on a patient in a cath lab. In one embodiment, environment 406 may also include inputs relating to a status of the site (e.g., the hospital or the cath lab), e.g., received from a building management system. For example, the status of the hospital may include information on possible issues or maintenance being performed in the hospital or cath lab, to thereby determine when the cath lab is not available.

In one embodiment, AI agent 402 is a deep neural network trained with deep reinforcement learning (DRL). In DRL, correct input/output pairs are not presented and sub-optimal actions are not explicitly correct. Instead, the focus is on online performance. In one embodiment, AI agent 402 may be trained based on real world training data supplemented with synthetic training data. Synthetic training data may be generated using rule-based or AI-based (e.g., generative adversarial networks) approaches to increase the size of the set of training data. Using synthetic training data to train AI agent 402 offers the following advantages: training data on a very large number of procedures can be automatically generated leading to an extensive set of training data; training data of complex procedures can be automatically generated; the cost of generating a large set of training data is reduced since the generation of synthetic data can be completely automated; training data of rare types of procedures can be obtained; the training data can be global or site-specific allowing AI agent 402 to account for specific local setups and configurations; and training AI agent 402 can be iteratively improved with more training data or better representations of the features.

AI agent 402 may be trained to schedule resources for a single site (e.g., single hospital or single cath lab) or may also be trained to schedule resources across multiple sites (e.g., multiple hospitals or multiple cath labs). In a multi-hospital environment, additional inputs into environment 406 may be taken into account, such as, e.g.: the time it would take for the patient to arrive at the hospital based on the location of the patient and current traffic conditions; the time it would take for the medical professionals to arrive at the hospital based on the location of the medical professional and current traffic conditions; and a location of a hospital room in which the patient current resides.

In one embodiment, AI agent 402 may be trained locally to account for individual characteristics of the medical professionals at the hospital. For example, the characteristics of the medical professionals at the hospital may include a level of experience of each medical professional, data regarding previous procedure times of the medical professionals for specific types of patients), specialization levels of each medical professional (e.g., whether they are trained to perform intravascular imaging or CTO interventions), or any other suitable characteristic.

Once trained, the trained AI agent 402 receives observations on an environment (e.g., a set of inputs defining a cath lab environment) and autonomously performs actions on that environment to optimally schedule resources according to the policy learned during training. The scheduling of resources may include, e.g., scheduling patients, scheduling medical professionals (e.g., doctors and nurses), scheduling stock material or consumables, or any other resource. Depending on how it was trained, the trained AI agent 402 may not necessarily find the optimal solution, but rather a good solution in near real-time.

In one embodiment, the trained AI agent 402 schedules all patients of a same type consecutively to optimize the overall time for performing the medical procedure. For example, the trained AI agent 402 may schedule all CTO interventions, all stable CAD single vessel cases, all stable CAD multi-vessel cases, or all ACS cases in a single day or during a continual interval of time.

In one embodiment, the trained AI agent 402 may receive real time updates (i.e., observations) on the environment. For example, the real time update may be sudden changes to the availability of medical professionals. In one embodiment, the real time updates may be provided by medical professionals (e.g., in patient care) via a social networking application, which displays the proposed work scheduled for each medical professional over a predefined period of time and allows the medical professional to propose changes to the schedule based on personal needs or preferences. Preferences of the medical professional may include, e.g., a preference for working or not working with specific medical professionals.

In one embodiment, the trained AI agent 402 receives a predicted workload of a cath lab to optimize scheduling of resources (e.g., to schedule a number of medical professionals or the work house of the medical professionals). The predicted workload of a cath lab may be predicted using a trained machine learning model. Such a trained machine learning model can be trained and applied similar to workflow 300 of FIG. 3. The trained machine learning model can be trained to predict workload of a cath lab based on training data such as, e.g., the number of stable patients admitted in the hospital, the number of patients scheduled for routine examinations, the current or predicted weather conditions (cold weather is associated with higher myocardial infarction rates, according to studies), and follow up visits planned based on previous examinations.

In one embodiment, the trained AI agent 402 receives a predicted likelihood of certain future events, such as, e.g., the likelihood that a patient will be readmitted due to comorbidities or reoccurrences of the disease. It is assumed that the event leading to the initial admission of the patient to the hospital is one of many events that could occur in the patient's history. By taking into account future events, AI agent 402 can schedule resources for performing a medical procedure on a patient to reduce the use of current and future resources (e.g., of the hospital).

The predicted likelihood of certain future events may be predicted using a trained machine learning model. The machine learning model may be trained and applied in a manner similar to workflow 300 of FIG. 3. The trained machine learning model is trained based on training data that includes outcome data. The outcome data may include, e.g., a number of cardiovascular events after patient discharge (e.g., cardiac death, reinfarction, revascularization), a quality of life after patient discharge (as assessed through, e.g., health surveys or questionnaires), or post-percutaneous coronary intervention measurements (e.g., FFR measurements in culprit lesions). The outcome data may be extracted using natural language processing and associated with each procedure in the training database.

In accordance with one embodiment, a computational model may be used to optimize (e.g., minimize) the administration of contrast agent to the patient (e.g., in the context of automated or programmable contrast injection). In particular, non-invasive medical images (e.g., CCTA) of the patient is acquired and an anatomical model of a region of interest is reconstructed (e.g., coronary arteries) from the medical images. A computational model is applied to compute hemodynamics and contrast agent propagation in the anatomical model of the coronary arteries. The computational model may be, e.g., a computational fluid dynamics model or an AI model. For example, the computation model may be a machine learning model trained to predict hemodynamics and contrast agent propagation using a set of training data (e.g., synthetic training data). An injection profile and injection time may be determined using the computed hemodynamics and propagation to provide optimal visualization of the arteries while minimizing contrast agent usage. Accordingly, contrast agent usage is minimized to optimize resource usage and the amount of contrast agent administered to the patient is also minimized.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-4. Certain steps or functions of the methods and workflows described herein, including one or more of the steps or functions of FIGS. 2-4, may be performed by a server or by another processor in a network-based cloud-computing system. Certain steps or functions of the methods and workflows described herein, including one or more of the steps of FIGS. 2-4, may be performed by a client computer in a network-based cloud computing system. The steps or functions of the methods and workflows described herein, including one or more of the steps of FIGS. 2-4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
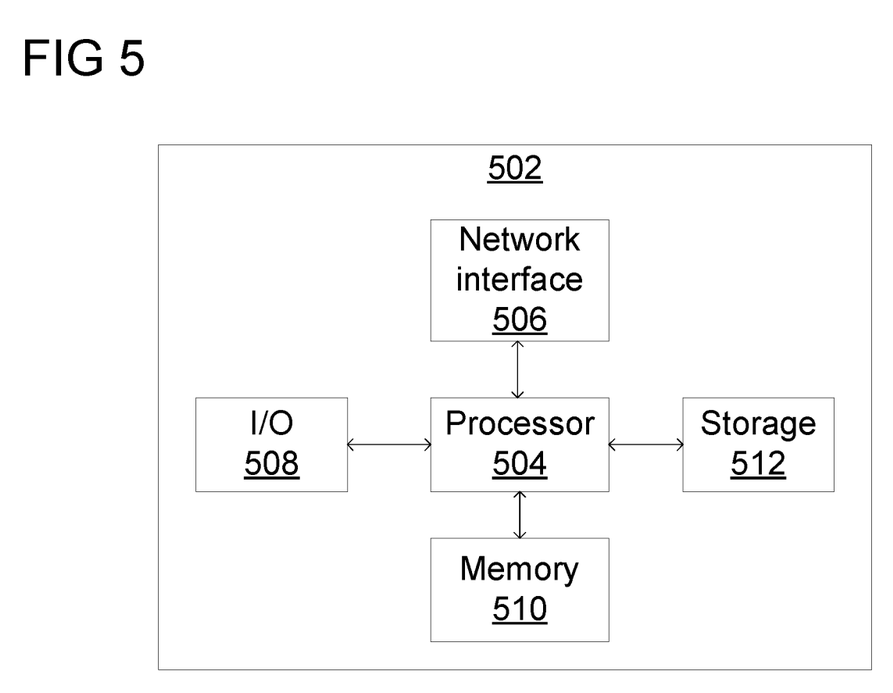
FIG. 5 shows a high-level block diagram of a computer.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIGS. 2-4 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIGS. 2-4. Accordingly, by executing the computer program instructions, the processor 504 executes the method and workflow steps or functions of FIGS. 2-4. Computer 504 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

Any or all of the systems and apparatus discussed herein, including elements of workstation 104, medical imaging system 106, and monitoring system 108 of FIG. 1, may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
 receiving a priori medical procedure data relating to a medical procedure to be performed on a patient in a catheterization laboratory;
 predicting one or more measures of interest based on the received a priori medical procedure data using a trained machine learning model, the one or more measures of interest comprising an overall time for performing the medical procedure on the patient in the catheterization laboratory and a time for performing specific portions of the medical procedure, wherein the trained machine learning model is trained to learn a mapping between the a priori medical procedure data and the one or more measures of interest based on medical procedure training data;
 generating personalized guidelines for performing the medical procedure to reduce the overall time for performing the medical procedure based on the received a priori medical procedure data using the trained machine learning model, wherein the personalized guidelines include 1) acquisition angles for acquiring medical imaging of the patient, 2) an order for investigating coronary arteries of the patient to minimize a usage of a contrast agent, and 3) a location for vascular access of the patient;
 determining an injection profile and an injection time using hemodynamics and a propagation of the contrast agent in the coronary arteries based on another trained machine learning model to minimize the usage of the contrast agent; and
 outputting the one or more predicted measures of interest.

2. The method of claim 1, wherein receiving a priori medical procedure data relating to a medical procedure to be performed on a patient in a catheterization laboratory comprises:
 receiving patient related medical procedure data comprising one or more of: medical images of the patient, measures extracted from the medical images of the patient, vascular access of the patient, a likelihood of the patient requiring intravascular imaging, a likelihood of the patient requiring invasive measurements, a type of the patient, laboratory test results of the patient, demographic information of the patient, and a history of the patient.

3. The method of claim 1, wherein receiving a priori medical procedure data relating to a medical procedure to be performed on a patient in a catheterization laboratory comprises:
 receiving non-patient related medical procedure data comprising one or more of: availability of medical professionals, devices used in the catheterization laboratory, a time associated with the medical procedure, and medical professionals scheduled to perform the medical procedure.

4. The method of claim 1, wherein the one or more measures of interest further comprise a complexity score associated with performing the medical procedure on the patient in the catheterization laboratory.

5. The method of claim 1, wherein the guidelines comprise one or more of: which coronary arteries are to be investigated, types of medical devices to be used during the medical procedure, and whether intravascular imaging is required.

6. The method of claim 1, further comprising:
generating guidelines for performing the medical procedure to reduce resource usage during the medical procedure on the patient in the catheterization laboratory using the trained machine learning model, the guidelines comprising one or more of: a number of medical devices to be used during the medical procedure and a number and type of medical professionals needed for performing the medical procedure.

7. The method of claim 1, further comprising:
automatically scheduling resources for performing the medical procedure on the patient in the catheterization laboratory based on the predicted one or more measures of interest using a trained artificial intelligence agent.

8. The method of claim 1, wherein outputting the one or more predicted measures of interest comprises:
displaying the one or more predicted measures of interest on a display device.

9. The method of claim 1, wherein the specific portions of the medical procedure comprise one or more of a patient preparation portion, a procedure start portion, an actual procedure portion, or a case completion portion.

10. An apparatus, comprising:
means for receiving a priori medical procedure data relating to a medical procedure to be performed on a patient in a catheterization laboratory;
means for predicting one or more measures of interest based on the received a priori medical procedure data using a trained machine learning model, the one or more measures of interest comprising an overall time for performing the medical procedure on the patient in the catheterization laboratory and a time for performing specific portions of the medical procedure, wherein the trained machine learning model is trained to learn a mapping between the a priori medical procedure data and the one or more measures of interest based on medical procedure training data;
means for generating personalized guidelines for performing the medical procedure to reduce the overall time for performing the medical procedure based on the received a priori medical procedure data using the trained machine learning model, wherein the personalized guidelines include 1) acquisition angles for acquiring medical imaging of the patient, 2) an order for investigating coronary arteries of the patient to minimize a usage of a contrast agent, and 3) a location for vascular access of the patient;
means for determining an injection profile and an injection time using hemodynamics and a propagation of the contrast agent in the coronary arteries based on another trained machine learning model to minimize the usage of the contrast agent; and
means for outputting the one or more predicted measures of interest.

11. The apparatus of claim 10, wherein the means for receiving a priori medical procedure data relating to a medical procedure to be performed on a patient in a catheterization laboratory comprises:
means for receiving patient related medical procedure data comprising one or more of: medical images of the patient, measures extracted from the medical images of the patient, vascular access of the patient, a likelihood of the patient requiring intravascular imaging, a likelihood of the patient requiring invasive measurements, a type of the patient, laboratory test results of the patient, demographic information of the patient, and a history of the patient.

12. The apparatus of claim 10, wherein the means for receiving a priori medical procedure data relating to a medical procedure to be performed on a patient in a catheterization laboratory comprises:
means for receiving non-patient related medical procedure data comprising one or more of: availability of medical professionals, devices used in the catheterization laboratory, a time associated with the medical procedure, and medical professionals scheduled to perform the medical procedure.

13. The apparatus of claim 10, wherein the one or more measures of interest further comprise a complexity score associated with performing the medical procedure on the patient in the catheterization laboratory.

14. The apparatus of claim 10, wherein the specific portions of the medical procedure comprise one or more of a patient preparation portion, a procedure start portion, an actual procedure portion, or a case completion portion.

15. A non-transitory computer readable medium storing computer program instructions, the computer program instructions when executed by a processor cause the processor to perform operations comprising:
receiving a priori medical procedure data relating to a medical procedure to be performed on a patient in a catheterization laboratory;
predicting one or more measures of interest based on the received a priori medical procedure data using a trained machine learning model, the one or more measures of interest comprising an overall time for performing the medical procedure on the patient in the catheterization laboratory and a time for performing specific portions of the medical procedure, wherein the trained machine learning model is trained to learn a mapping between the a priori medical procedure data and the one or more measures of interest based on medical procedure training data;
generating personalized guidelines for performing the medical procedure to reduce the overall time for performing the medical procedure based on the received a priori medical procedure data using the trained machine learning model, wherein the personalized guidelines include 1) acquisition angles for acquiring medical imaging of the patient, 2) an order for investigating coronary arteries of the patient to minimize a usage of a contrast agent, and 3) a location for vascular access of the patient;
determining an injection profile and an injection time using hemodynamics and a propagation of the contrast agent in the coronary arteries based on another trained machine learning model to minimize the usage of the contrast agent; and
outputting the one or more predicted measures of interest.

16. The non-transitory computer readable medium of claim 15, wherein the guidelines comprise one or more of: which coronary arteries are to be investigated, types of medical devices to be used during the medical procedure, and whether intravascular imaging is required.

17. The non-transitory computer readable medium of claim 15, the operations further comprising:
generating guidelines for performing the medical procedure to reduce resource usage during the medical procedure on the patient in the catheterization laboratory using the trained machine learning model, the guidelines comprising one or more of: a number of medical devices to be used during the medical procedure and a number and type of medical professionals needed for performing the medical procedure.

18. The non-transitory computer readable medium of claim 15, the operations further comprising:
automatically scheduling resources for performing the medical procedure on the patient in the catheterization laboratory based on the predicted one or more measures of interest using a trained artificial intelligence agent.

19. The non-transitory computer readable medium of claim 15, wherein outputting the one or more predicted measures of interest comprises:
displaying the one or more predicted measures of interest on a display device.

20. The non-transitory computer readable medium of claim 15, wherein the specific portions of the medical procedure comprise one or more of a patient preparation portion, a procedure start portion, an actual procedure portion, or a case completion portion.

\* \* \* \* \*